(12) United States Patent
Hollis et al.

(10) Patent No.: US 8,057,485 B2
(45) Date of Patent: Nov. 15, 2011

(54) SPECIMEN RETRIEVAL DEVICE

(75) Inventors: Jeffrey D. Hollis, Gallatin, TN (US);
Gregpru D. Hollis, Nashville, TN (US);
John Troy Wilson, Nashville, TN (US)

(73) Assignee: The Hollis Group, Lebanon, TN (US)

( * ) Notice: Subject to any disclaimer, the term of this patent is extended or adjusted under 35 U.S.C. 154(b) by 797 days.

(21) Appl. No.: 11/835,671

(22) Filed: Aug. 8, 2007

(65) Prior Publication Data

US 2008/0221588 A1    Sep. 11, 2008

Related U.S. Application Data

(60) Provisional application No. 60/893,332, filed on Mar. 6, 2007.

(51) Int. Cl.
*A61B 17/24* (2006.01)
*A61B 17/26* (2006.01)
(52) U.S. Cl. ............................................ 606/114
(58) Field of Classification Search .................. 606/110, 606/113, 114, 127, 128; 604/317, 318
See application file for complete search history.

(56) References Cited

U.S. PATENT DOCUMENTS

| 5,354,303 | A | 10/1994 | Spaeth et al. |
| 5,647,372 | A | 7/1997 | Tovey et al. |
| 5,971,995 | A | 10/1999 | Rousseau |
| 6,383,197 | B1 | 5/2002 | Conlon et al. |
| 2002/0151955 | A1* | 10/2002 | Tran et al. ................ 623/1.12 |
| 2004/0138587 | A1 | 7/2004 | Lyons, IV |
| 2006/0004376 | A1* | 1/2006 | Shipp et al. .................. 606/99 |
| 2007/0088370 | A1* | 4/2007 | Kahle et al. .................. 606/114 |
| 2008/0077154 | A1* | 3/2008 | Edwards et al. .............. 606/105 |

FOREIGN PATENT DOCUMENTS

| EP | 0947166 | 10/1999 |
| WO | WO 2004/064669 | 8/2004 |
| WO | 2007048085 | 4/2007 |

* cited by examiner

*Primary Examiner* — Ryan Severson
*Assistant Examiner* — Katherine M Shi
(74) *Attorney, Agent, or Firm* — Sturm & Fix LLP

(57) ABSTRACT

The present invention provides a surgical specimen retrieval device that allows one-handed use by incorporating a geared spool to amplify take up of a flexible line to close the mouth of the specimen bag after the surgical specimen is deposited in the bag. The retrieval device includes a spool with an attached gear that is rotated by movement of a deployment rod with serrated teeth. A flexible line has a proximal end attached to the spool and the distal end attached to the mouth of the bag. When the deployment reel is moved from an extended position to an inserted position, the spool rotates and pays out flexible line to allow the mouth of the deployed bag to open. Once a specimen is taken and deposited in the bag, the deployment rod is moved from the inserted position toward the extended position. This rod movement rotates the spool to take up the line and close the mouth of the bag. When the rod is moved to a fully retracted position, the teeth on the rod disengage from the gear, which allows the spool to rotate freely. The device is then removed from the trocar and the line is used to pull the bagged specimen from the body cavity.

2 Claims, 5 Drawing Sheets

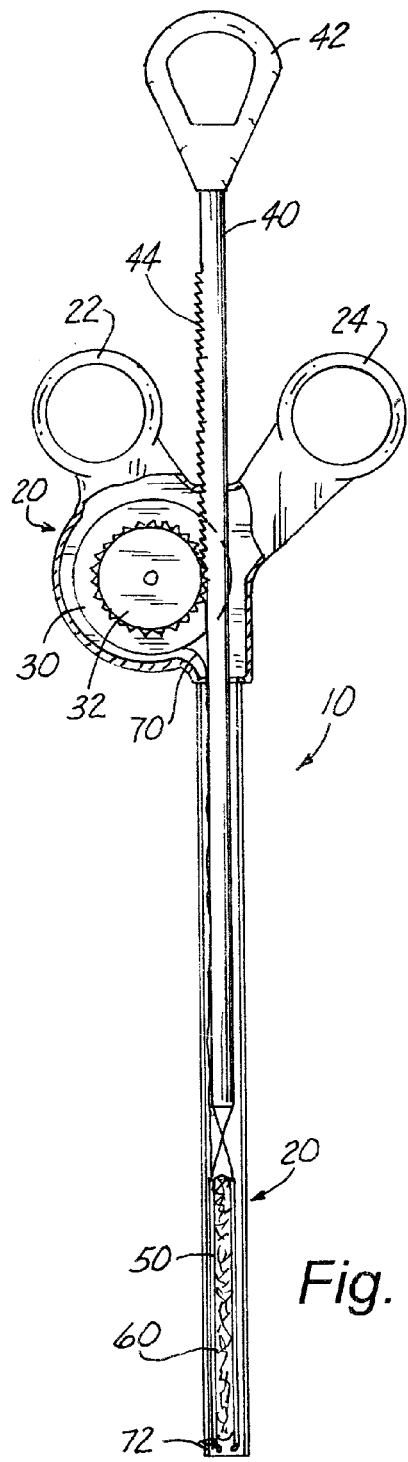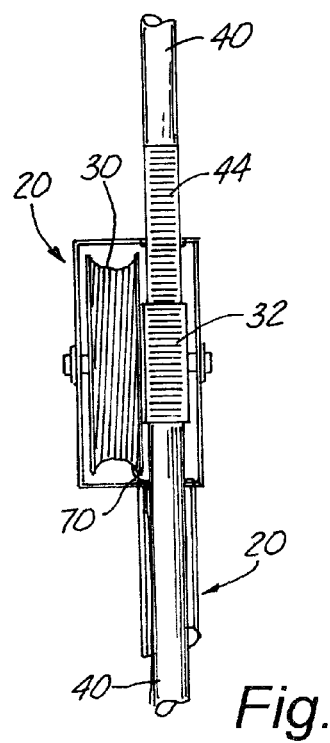
Fig. 3
Fig. 4

SPECIMEN RETRIEVAL DEVICE

CROSS REFERENCE TO RELATED APPLICATIONS

This application claims the benefit of U.S. Provisional Patent Application Ser. No. 60/893,332 filed Mar. 6, 2007 entitled "ONE HANDED MINIMALLY INVASIVE SPECIMEN RETRIEVAL DEVICE WITH SPOOL/GEAR MECHANISM", which is incorporated herein by reference.

BACKGROUND OF THE INVENTION

1. Field of the Invention

The present invention relates to the field of surgical instruments, and more particularly to a specimen retrieval device for use in minimally invasive surgery to retrieve a specimen from a body cavity.

2. Description of Related Art

As can be seen by reference to the following U.S. Pat. Nos. 5,354,303; 5,647,372; 5,971,995; 6,383,197; WO04064669; and U.S. Publn. 20040138587, the prior art is replete with myriad and diverse specimen retrieval devices.

While all of the aforementioned prior art constructions are more than adequate for the basic purpose and function for which they have been specifically designed, they are uniformly deficient with respect to their failure to provide a simple, efficient, and practical specimen retrieval device that may be operated with one hand.

As a consequence of the foregoing situation, there has existed a longstanding need for a new and improved specimen retrieval device, and the provision of such a device is a stated objective of the present invention.

BRIEF SUMMARY OF THE INVENTION

Briefly stated, the present invention provides a surgical specimen retrieval device that allows one-handed use by incorporating a geared spool to amplify take up of a flexible line to close the mouth of the specimen bag after the surgical specimen is deposited in the bag. The retrieval device includes a spool with an attached gear that is rotated by movement of a deployment rod with serrated teeth. A flexible line has a proximal end attached to the spool and the distal end attached to the mouth of the bag. When the deployment reel is moved from an extended position to an inserted position, the spool rotates and pays out flexible line to allow the mouth of the deployed bag to open. Once a specimen is taken and deposited in the bag, the deployment rod is moved from the inserted position toward the extended position. This rod movement rotates the spool to take up the line and close the mouth of the bag. When the rod is moved to a fully retracted position, the teeth on the rod disengage from the gear, which allows the spool to rotate freely. The device is then removed from the trocar and the line is used to pull the bagged specimen from the body cavity.

BRIEF DESCRIPTION OF THE SEVERAL VIEWS OF THE DRAWINGS

These and other attributes of the invention will become more clear upon a thorough study of the following description of the best mode for carrying out the invention, particularly when reviewed in conjunction with the drawings, wherein:

FIG. 3 is a sectional view taken along line 3-3 of FIG. 1;

FIG. 4 is a sectional view taken along line 4-4 of FIG. 1;

DETAILED DESCRIPTION OF THE INVENTION

Figure 1:
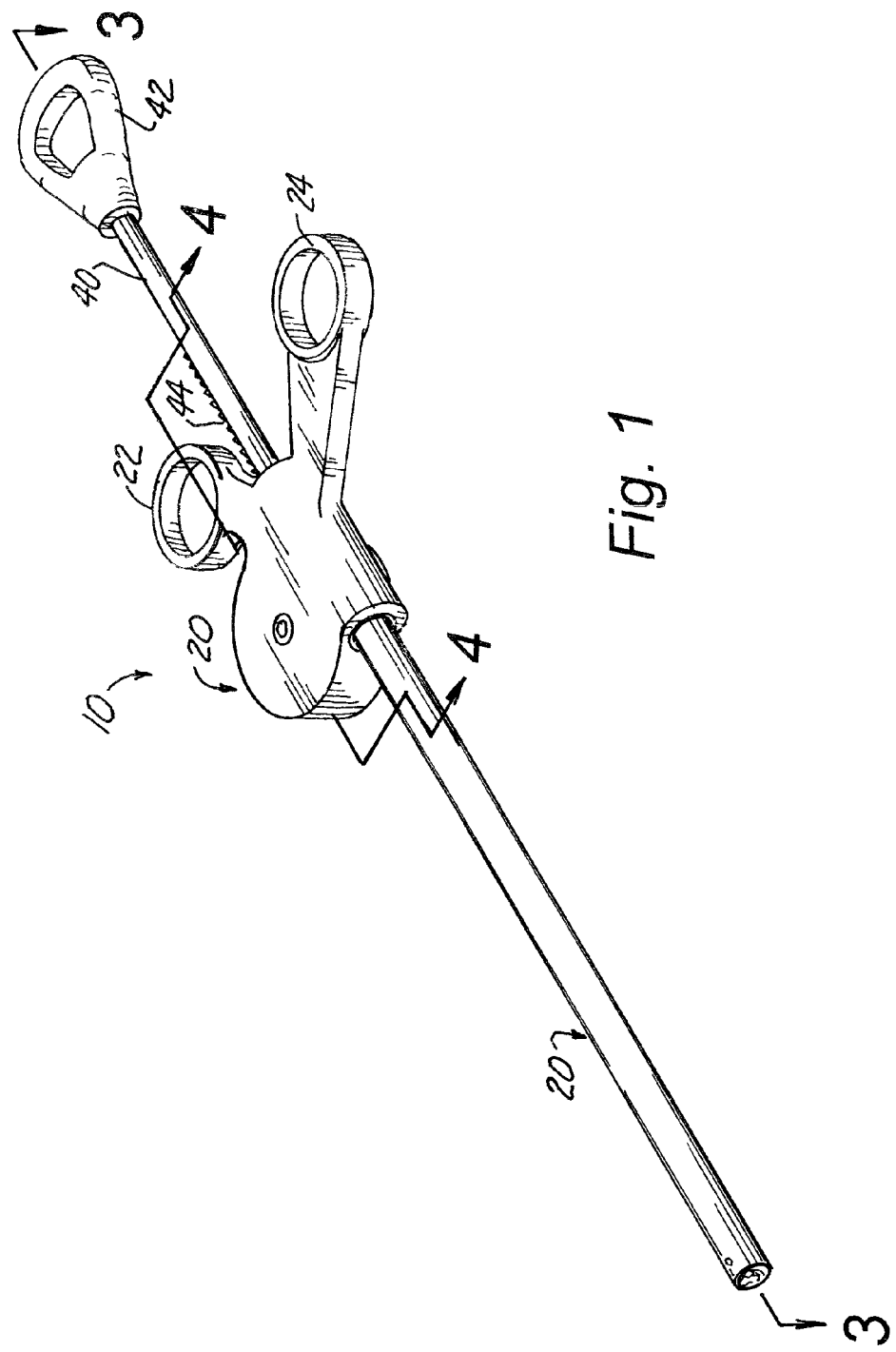
FIG. 1 is a perspective view of the specimen retrieval device of the present invention.
Figure 2:
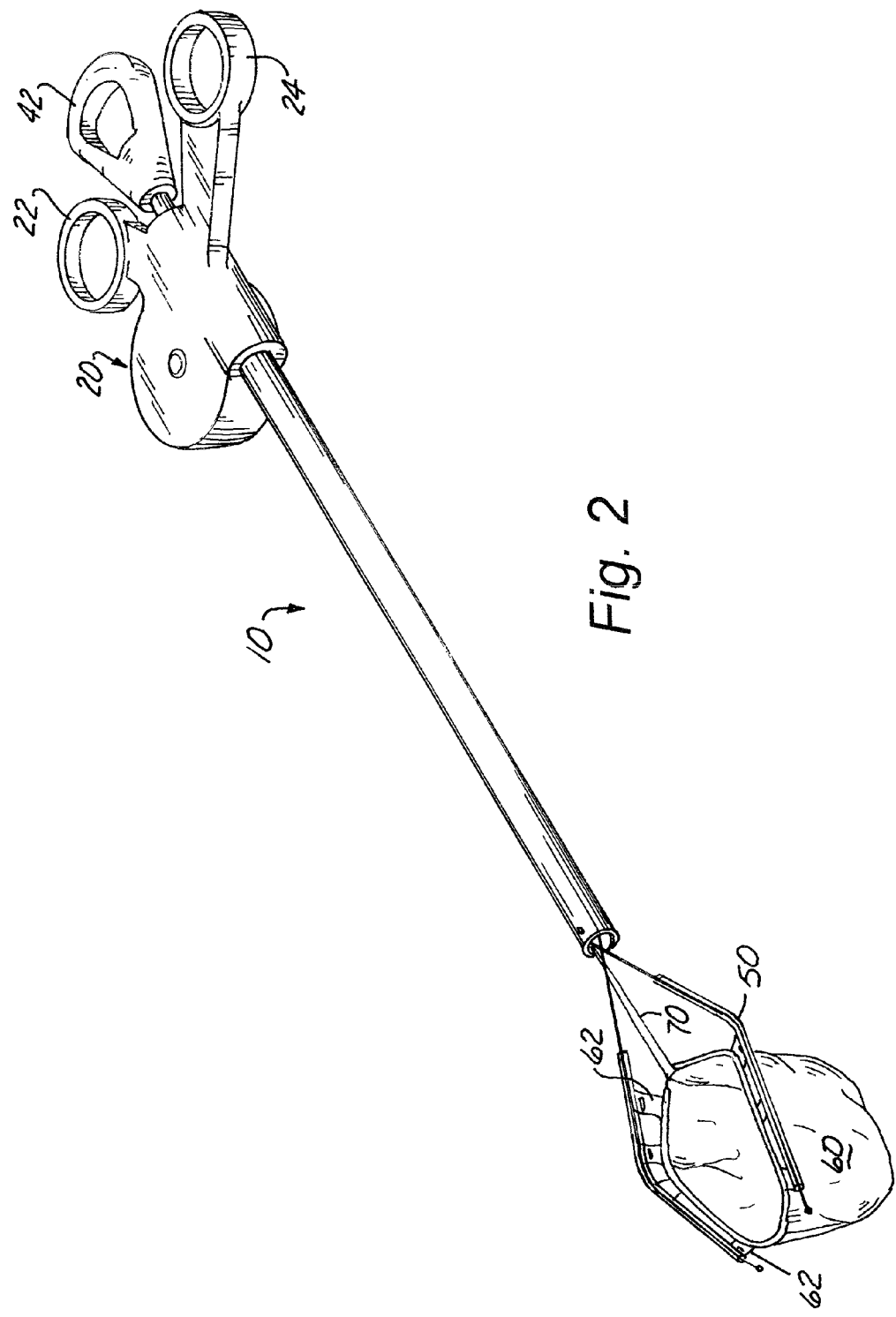
FIG. 2 is a perspective view similar to FIG. 1 but showing the specimen bag ejected from the housing.

As can be seen by reference to the drawings, and in particular to FIG. 1, the specimen retrieval device that forms the basis of the present invention is designated generally by the reference number 10.

The components of this invention include the main housing 20 which contains a spool 30, a gear wheel 32 that interacts with a serrated deployment rod 40, a serrated deployment rod 40 with a self expanding rigid loop 50 attached to the distal end, a specimen retrieval bag 60 attached to the self expanding rigid loop 50, and a string 70 attached to the spool 30 and the bag 60. The main housing 20 is made of rigid plastic and is shaped like a long tube that is larger on the proximal end to accommodate the spool 30 and attached gear mechanism 32, and the deployment rod 40. The housing 20 includes finger holes 22, 24 for grasping the instrument 10 with the second and third fingers. The deployment shaft 40 is a long rigid plastic rod with a finger hole 42 for the thumb. It enters the housing 20 from the proximal end. On the shaft of the rod 40 are teeth serrations 44 that interact with the gear wheel 32 to produce unwinding of the string 70 on the deployment, and closure of the bag 60 upon retraction. On the distal end of the rod 40, a blunt ended rigid pre-stressed loop 50 of metal or plastic is attached. This holds the plastic polyester specimen bag 60, and when deployed out of the housing 20 opens the mouth of the bag 60. The gear wheel 32 interacts with the serrations 44 on the deployment rod 40 to deploy, and then close the attached bag 60. A silk or nylon string 70 is attached to the spool 30 proximally, and is attached to the mouth of the bag 60 distally, and runs the length of the device internally. A slip knot 72 of the string 70 facilitates bag closure with retraction of the rod 40.

Figure 5:
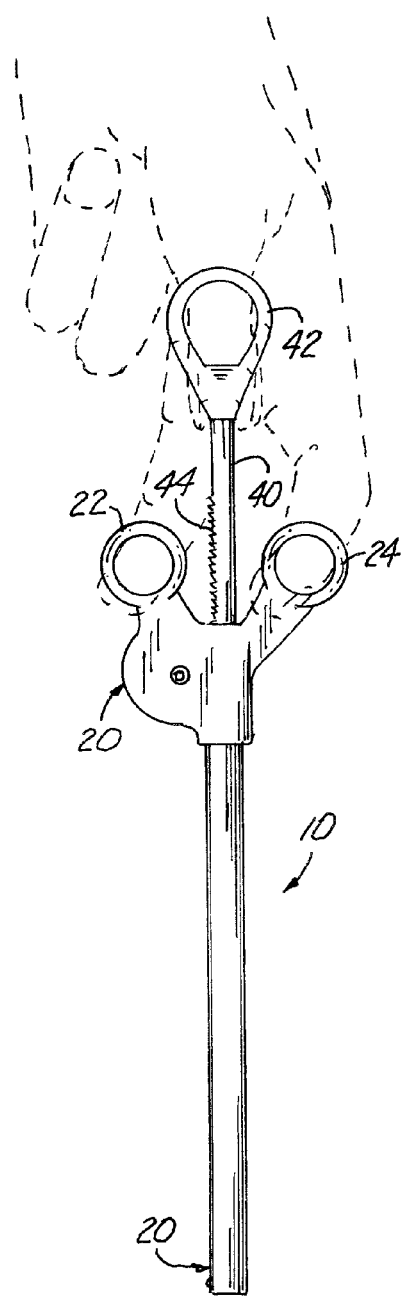
FIG. 5 is a side elevational view of the device.
Figure 6:
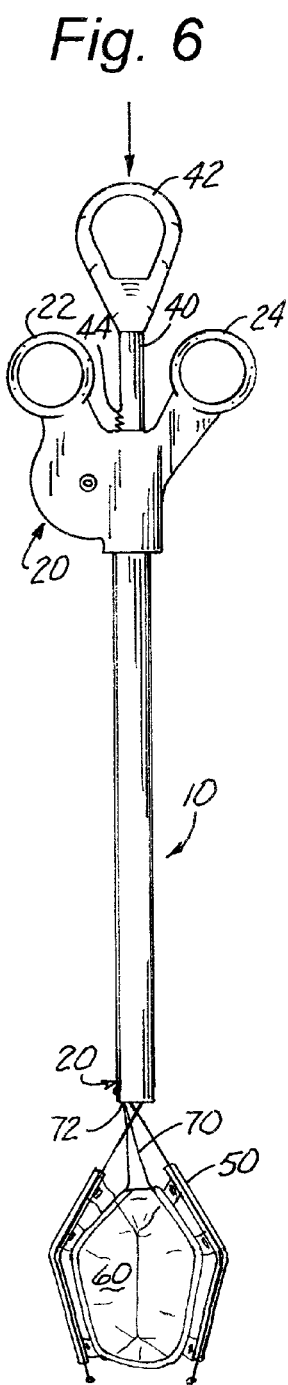
FIG. 6 is a side elevational view similar to FIG. 5, but showing the specimen bag ejected.
Figure 7:
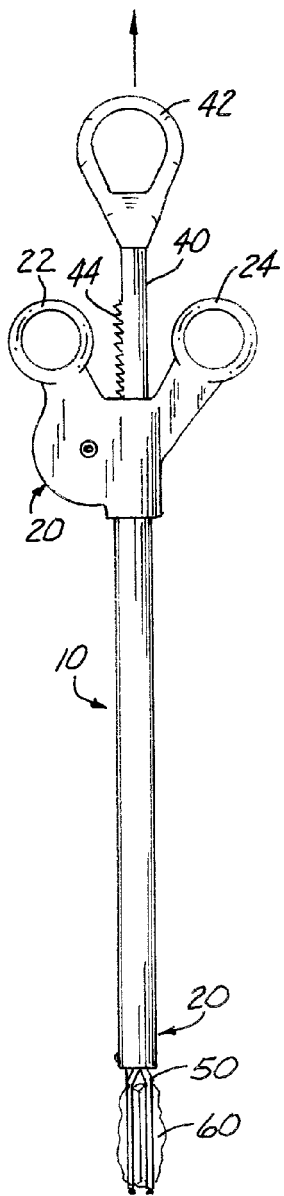
FIG. 7 is a side elevational view similar to FIGS. 5 and 6, but showing the mouth of the specimen bag closed.
Figure 8:
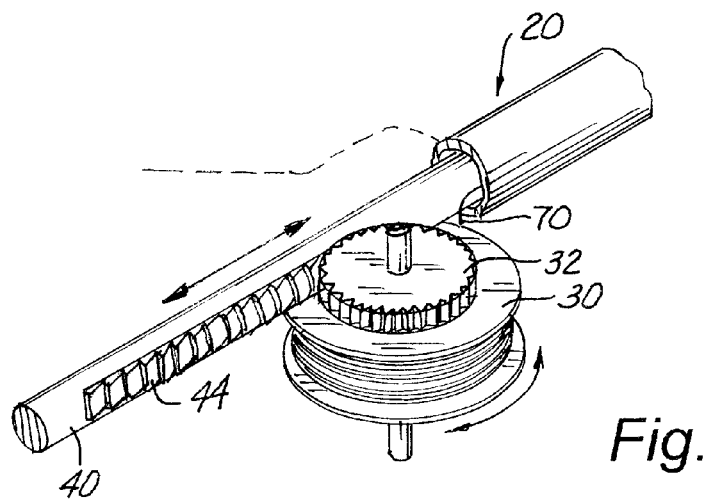
FIG. 8 is an enlarged partial perspective view with portions of the housing cut away to show the spool with attached gear, and the mating serrated teeth on the deployment rod.
Figure 9:
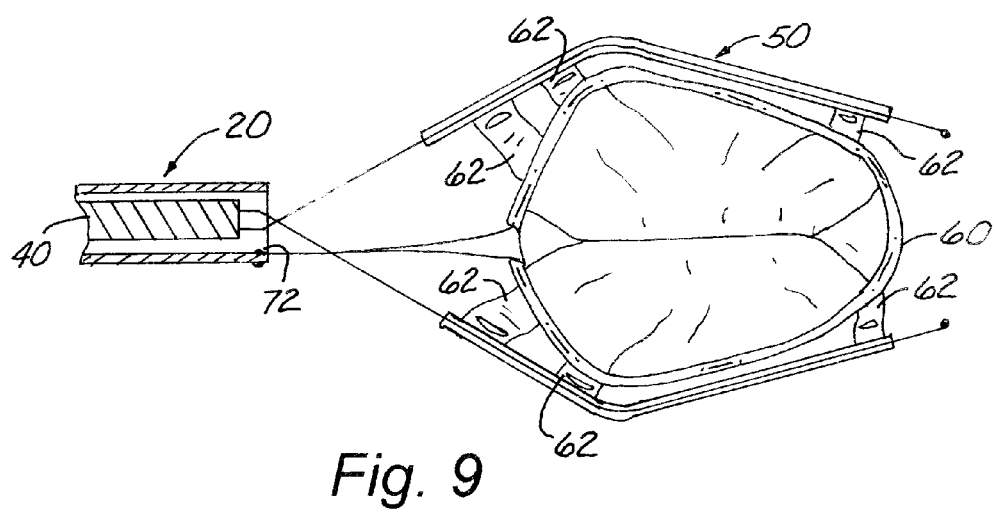
FIG. 9 is an enlarged partial side elevational view of the deployed specimen bag, with a sectional showing of the distal end of the housing.

In use, the device 10 is first inserted into a minimally invasive trocar. Deployment of the bag 60 is accomplished by moving the rod 40 from its extended position (FIG. 5) toward its inserted position (FIG. 6) in a syringe type motion. This motion causes unwinding or paying out of the string 70 on the pre-wound spool 30 due to the interaction of the serrations on the deployment rod 30 and the gear 32. The string 70 is attached proximally to the spool 30 and runs the length of the housing 20 internally to the bag 60 distally. The bag 60 is pushed out of the housing 20 distally. The pre-stressed loop 50 opens the mouth of the bag 60 upon exiting the housing 20. A specimen is then inserted and held within the bag 60. Retraction of the deployment rod 40 interacts with the gear 32 to transfer power to the spool 30 to amplify string retraction resulting in a shorter than currently available required retraction length of the rod 40. A slip knot 72 near the mouth of the bag 60 is used to cinch the mouth of the bag 60 closed while the string 70 is collected or taken up on the spool 30. Loose attachments 62 of the bag 60 to the loop 50 are overcome upon bag closure to separate the bag 60 from the loop 50. Upon full retraction, the serrations 44 on the deployment rod 40 and gear 32 are disengaged allowing the spool 30 to freely unwind. This allows the entire housing 20 to be removed from the trocar leaving only the string 70 entering the trocar. The string 70 is then used to pull the bag 60 and specimen out of the body cavity.

The objective of the device is to allow one-handed closure of the specimen bag to permit easy removal of the minimally invasive specimen. Current models are awkward and ergonomically inferior. Current bags require two hands to close the bag and thus are difficult to use. Thus, the surgeon must let go of the actual specimen or have an assistant close the bag for them. One-handed use allows cinching the bag down around the specimen in a controlled manner. This facilitates removal because the specimen can be easily cinched in the mouth of the bag, if desired, to make it aerodynamic. The unique design is also more ergonomic and less frustrating. This device will save time with specimen removal from the body cavity. The design improves over instruments that currently exist by allowing improved specimen handling and one-handed closure without outside assistance.

This device achieves it objective through a unique spool/gear mechanism to facilitate bag closure. The spool/gear mechanism is attached to a string which is used to close the mouth of the specimen retrieval bag. The gear-wheel mechanism amplifies string collection to allow a shorter stroke on the device closure hardware. This allows a simpler shorter movement to allow one-handed closure. Current devices require long retraction lengths that cannot easily be done with one hand.

This invention is for laparoscopic specimen retrieval. It may also be used in any minimally invasive surgery in which a specimen needs to be retrieved from a body cavity, for example, thoracoscopy.

This invention can be structured to different sizes to accommodate the specific need. Larger bags for larger specimens. Longer or shorter shafts for different body cavities. Larger or smaller hand pieces for men or women surgeons. Different diameter shafts to fit through different sized access trocars. The gear wheel mechanism can be adjusted to allow greater or lesser amplification for a given movement, for example, a small gear and larger spool to maximize string retraction.

Although only an exemplary embodiment of the invention has been described in detail above, those skilled in the art will readily appreciate that many modifications are possible without materially departing from the novel teachings and advantages of this invention. Accordingly, all such modifications are intended to be included within the scope of this invention as defined in the following claims.

Having thereby described the subject matter of the present invention, it should be apparent that many substitutions, modifications, and variations of the invention are possible in light of the above teachings. It is therefore to be understood that the invention as taught and described herein is only to be limited to the extent of the breadth and scope of the appended claims.

We claim:

1. A surgical specimen retrieval device, comprising:
    a housing having an enlarged proximal end and an elongated tubular portion extending from the enlarged end;
    a pair of spaced finger openings disposed to extend back from the proximal end of the housing; a spool including a toothed gear rotatably mounted within the enlarged proximal end laterally offset from the elongated tubular portion;
    an elongated deployment rod slidably received within the elongated tubular portion of the housing, the deployment rod having a proximal end and a distal end and serrated teeth carried on a portion of the deployment rod extending from a point near the proximal end to a point intermediate the proximal end and the distal end of the rod, the serrated teeth being disposed to engage the toothed gear on the spool, the deployment rod being movable from an extended position to an inserted position and then to a fully retracted position;
    a thumb opening disposed to extend back from the proximal end of the deployment rod;
    a pre-stressed loop disposed to extend forward from the distal end of the deployment rod;
    a specimen bag having a closable mouth, the bag being removably attached to the pre-stressed loop by interconnecting loose attachments, wherein the bag is initially disposed within the elongated tubular portion of the housing near its distal end, and wherein movement of the deployment rod from the extended position to the inserted position ejects the bag from the distal end of the tubular portion of the housing;
    a flexible line having a proximal end releasable secured to the spool and a distal end attached to the mouth of the bag;
    wherein the serrated teeth of the deployment rod are disposed to matingly engage the toothed gear of the spool when the deployment rod is in the extended and inserted positions, and the serrated teeth disengage from the gear when the deployment rod is in the fully retracted position, and movement of the deployment rod from the extended position toward the inserted position rotates the spool to pay out the flexible line, movement of the deployment rod from the inserted position toward the extended position rotates the spool to take up the flexible line and close the mouth of the bag, and movement of the deployment rod to the fully retracted position allows the spool to freely unwind to release the proximal end of the flexible line from the spool allowing the proximal end of the flexible line to exit the distal end of the tubular portion of the housing.

2. The specimen retrieval device of claim 1 wherein the flexible line is a heavy silk or nylon string.

* * * * *